United States Patent [19]
Ludewigt et al.

[11] Patent Number: 5,438,454
[45] Date of Patent: Aug. 1, 1995

[54] METHOD FOR SELECTING MINIMUM WIDTH OF LEAF IN MULTILEAF ADJUSTABLE COLLIMATOR WHILE INHIBITING PASSAGE OF PARTICLE BEAMS OF RADIATION THROUGH SAWTOOTH JOINTS BETWEEN COLLIMATOR LEAVES

[75] Inventors: Bernhard Ludewigt, Berkeley; John Bercovitz, Hayward; Mark Nyman, Berkeley; William Chu, Lafayette, all of Calif.

[73] Assignee: Regents, University of California, Berkeley, Calif.

[21] Appl. No.: 146,503

[22] Filed: Nov. 1, 1993

[51] Int. Cl.6 .................................................. B32B 3/28
[52] U.S. Cl. ...................... 359/641; 378/145; 250/505.1
[58] Field of Search ............ 359/641, 831, 832, 833, 359/834, 835, 836, 837; 378/149, 150, 151; 250/505.1

[56] References Cited

U.S. PATENT DOCUMENTS

| | | | |
|---|---|---|---|
| 4,465,540 | 8/1984 | Albert | 152/252 |
| 5,204,160 | 4/1993 | Rouser | 428/167 |

OTHER PUBLICATIONS

Itano, Akifumi, et al., eds., *Proceedings of the NIRS International Workshop on Heavy Charged Particle Therapy and Related Subjects*, Jul. 4–5, 1991, pp. 115–116.

*Primary Examiner*—Scott J. Sugarman
*Assistant Examiner*—Ricky Mack
*Attorney, Agent, or Firm*—Paul R. Martin

[57] ABSTRACT

A method is disclosed for selecting the minimum width of individual leaves of a multileaf adjustable collimator having sawtooth top and bottom surfaces between adjacent leaves of a first stack of leaves and sawtooth end edges which are capable of intermeshing with the corresponding sawtooth end edges of leaves in a second stack of leaves of the collimator. The minimum width of individual leaves in the collimator, each having a sawtooth configuration in the surface facing another leaf in the same stack and a sawtooth end edge, is selected to comprise the sum of the penetration depth or range of the particular type of radiation comprising the beam in the particular material used for forming the leaf; plus the total path length across all the air gaps in the area of the joint at the edges between two leaves defined between lines drawn across the peaks of adjacent sawtooth edges; plus at least one half of the length or period of a single sawtooth. To accomplish this, in accordance with the method of the invention, the penetration depth of the particular type of radiation in the particular material to be used for the collimator leaf is first measured. Then the distance or gap between adjoining or abutting leaves is selected, and the ratio of this distance to the height of the sawteeth is selected. Finally the number of air gaps through which the radiation will pass between sawteeth is determined by selecting the number of sawteeth to be formed in the joint. The measurement and/or selection of these parameters will permit one to determine the minimum width of the leaf which is required to prevent passage of the beam through the sawtooth joint.

11 Claims, 3 Drawing Sheets

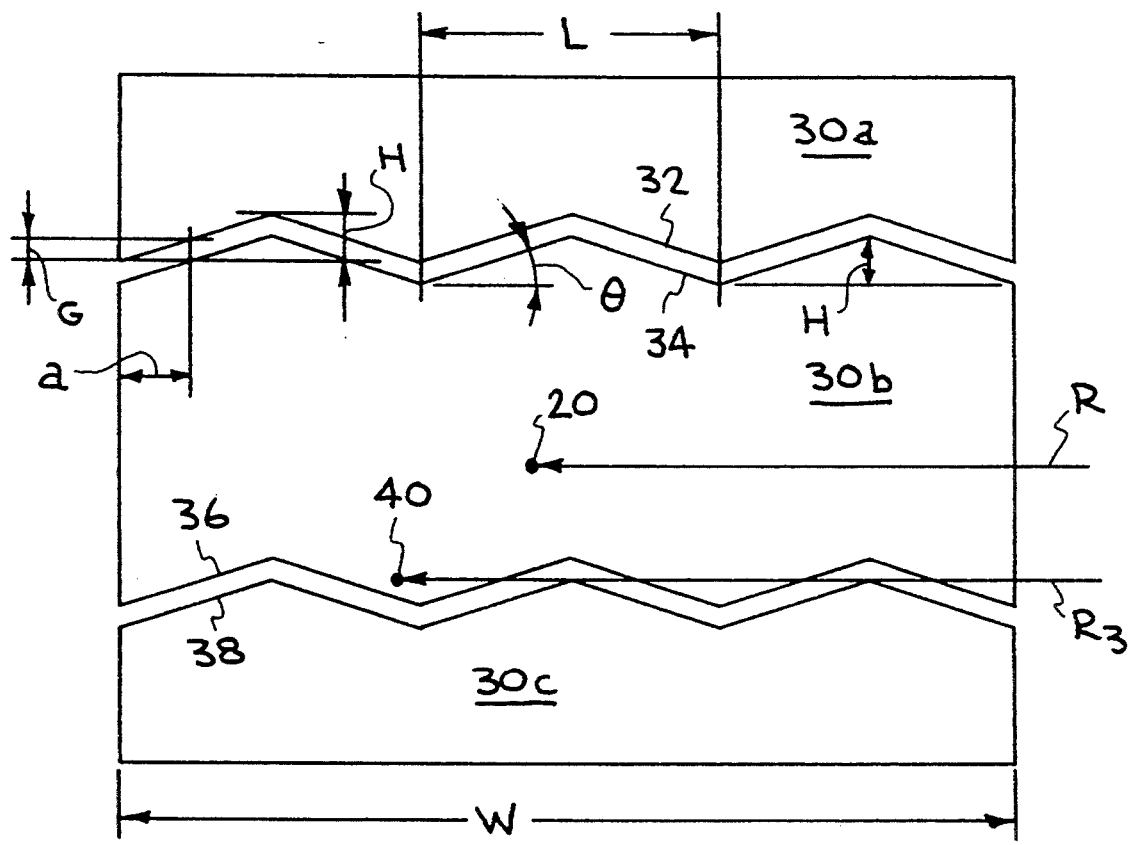
FIG. 3
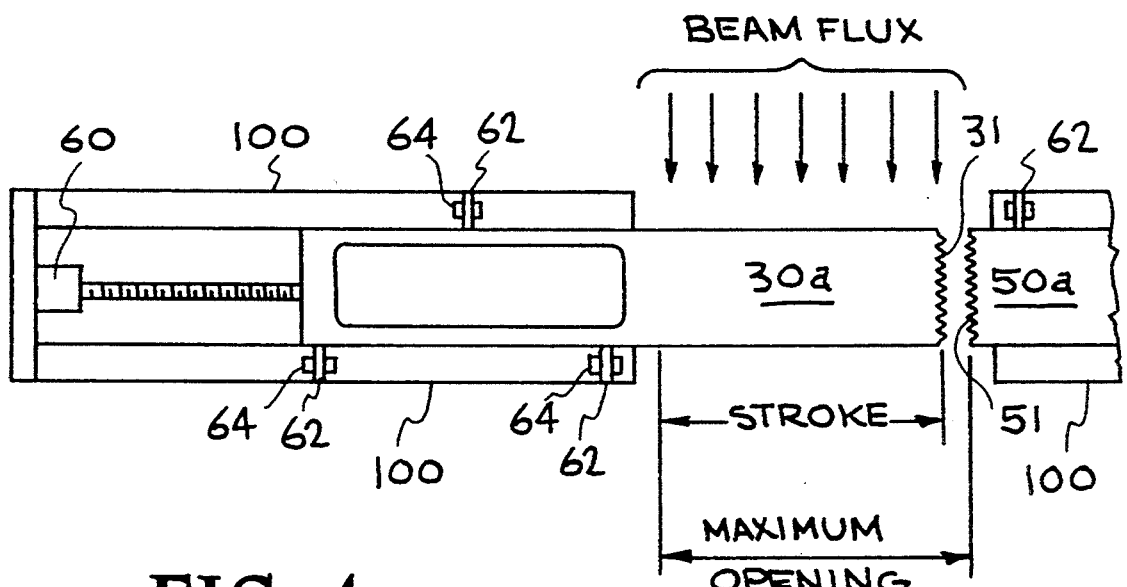
FIG. 4
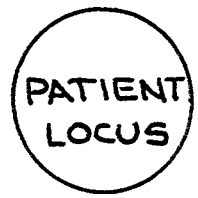

```
┌─────────────────────────────────────────────┐
│ MEASURING THE PENETRATION DEPTH OF THE      │
│ RADIATION BEAM THROUGH A SOLID PORTION      │
│ OF THE COLLIMATOR LEAF MATERIAL             │
└─────────────────────────────────────────────┘
                      │
┌─────────────────────────────────────────────┐
│ SELECTING A GAP BETWEEN ADJACENT OR         │
│ ABUTTING LEAVES OF THE COLLIMATOR           │
└─────────────────────────────────────────────┘
                      │
┌─────────────────────────────────────────────┐
│ SELECTING A VALUE FOR THE HEIGHT OF THE     │
│ SAWTEETH OF 2 TO 10 TIMES THE SELECTED GAP  │
└─────────────────────────────────────────────┘
                      │
┌─────────────────────────────────────────────┐
│ SELECTING THE NUMBER OF SAWTEETH            │
│ FOR THE JOINT BETWEEN ADJACENT OR           │
│ ABUTTING LEAVES OF THE COLLIMATOR           │
└─────────────────────────────────────────────┘
                      │
┌─────────────────────────────────────────────┐
│ DETERMINING THE MINIMUM WIDTH OF THE        │
│ COLLIMATOR LEAF BASED ON THE                │
│ PENETRATION DEPTH OF THE RADIATION BEAM,    │
│ THE SELECTED GAP BETWEEN THE LEAVES,        │
│ THE NUMBER OF SAWTEETH IN THE JOINT, AND    │
│ THE HEIGHT OF THE SAWTEETH                  │
└─────────────────────────────────────────────┘
```

FIG. 5

METHOD FOR SELECTING MINIMUM WIDTH OF LEAF IN MULTILEAF ADJUSTABLE COLLIMATOR WHILE INHIBITING PASSAGE OF PARTICLE BEAMS OF RADIATION THROUGH SAWTOOTH JOINTS BETWEEN COLLIMATOR LEAVES

BACKGROUND OF THE INVENTION

The invention described herein arose in the course of, or under, Contract No. DE-AC03-SF00098 between the United States Department of Energy and the University of California for the operation of the Lawrence Berkeley Laboratory.

1. Field of the Invention

This invention relates to a method of making a multileaf collimator for radiation beams such as, for example, heavy charged particle beams used in the treatment of cancer by radiation. More particularly, this invention relates to a method for minimizing the width of the leaves when making sawtooth joints between leaves of a multileaf collimator which provides an adjustable aperture while still preventing leakage of radiation between the leaves.

2. Description of the Related Art

In the treatment of cancer by radiation, a shield is conventionally placed between the patient and the radiation source to provide limited exposure of the patient to the radiation beam. The size of the shield varies with the size of the area to be irradiated, as well as the size of the patient. For this reason, the use of an adjustable collimator, i.e., a collimator with adjustable leaves, has been previously proposed. However, the use of an adjustable collimator introduces the additional problem of possible radiation leakage through the cracks or joints between adjacent leaves. In the published Proceedings of the NIRS International workshop on Heavy Charged Particle Therapy and Related Subjects, Jul. 4-5, 1991 National Institute of Radiological Sciences, on pages 115-116, there is described a multileaf collimator having a number of independently adjustable leaves on each side of the collimator, as shown in FIG. 1. Such a collimator is rotatable 90 degrees around the central axis of the radiation beam, and the leaves can be operated horizontally, vertically, or at any angle therebetween, thus allowing the collimation of almost all field shapes encountered in radiation therapy.

In the adjustable collimator generally shown at 2 in FIG. 1, a first stack of independently adjustable leaves $4a-4p$ is positioned on one side of the beam path, and a second opposed set of independently adjustable leaves $6a-6p$ is positioned on the opposite side of the beam path. Each leaf slides along a track (not shown) and the motion of each leaf is independently controlled by its own DC motor means $8a-8p$ and $10a-10p$. The result, as shown in FIG. 1, is an adjustable opening which can be tailored to the individual size of the patient and treatment area on that patient. While such an adjustable collimator greatly increases the flexibility of patterning the opening to various sizes and shapes, it will be immediately apparent that such adjustability creates a potential problem of radiation leakage through the joints between adjacent adjustable leaves. In the NIRS Proceedings publication, the authors state that the adjacent surfaces of the leaves may be shaped in a sawtooth pattern, to inhibit particles from leaking through such joints or cracks between the leaves. The authors further mention that such a corrugated geometry has been tested with helium and neon ion beams, with no film detection of particle leakage through the cracks. However, the use of such a sawtooth configuration for the mating surfaces of adjacent leaves, as illustrated in FIG. 2, can greatly increase the required total width of each leaf, depending upon the configuration of the sawtooth edge and the gap G between the respective sawtooth surfaces of adjacent leaves. In FIG. 2, leaf $4a$ is shown with sawtooth edges $12a$ and $12b$, $14a$ and $14b$, $16a$ and $16b$, and $18a$ and $18b$ which face mating sawtooth edges $22a$ and $22b$, $24a$ and $24b$, $26a$ and $26b$, and $28a$ and $28b$ in adjacent leaf $4b$ in the same stack. When a radiation beam, as shown at beam path R, of a given intensity or energy, penetrates the solid portion of leaves $4a$ or $4b$, the normally penetrates to some distance, as shown as point 20, which must be less than the total thickness of leaves $4a$ and $4b$ for the shielding to be effective. However, the width of leaves $4a$ and $4b$ must be wider than this penetration depth of beam path R if beams penetrating the stack of leaves at a joint, such as shown at beam paths $R_1$ and $R_2$ in FIG. 2, are also to be completely shielded, because only portions of the $R_1$ and $R_2$ beam paths pass through shielding material of leaves $4a$ and $4b$, with the remainder of the $R_1$ and $R_2$, beam paths passing through air, as shown by the dotted lines, i.e., with no attenuation of the beams. It will also be noted, by examining FIG. 2, that the respective beam paths denoted in the Figure as $R_1$ and $R_2$, are drawn to coincide with the tips of the respective saw teeth to illustrate the area, between lines $R_1$ and $R_2$, wherein the beam path through air is maximized and the beam path through the shielding material of the leaves is minimized.

As shown in FIG. 2, for beam $R_1$ or $R_2$ to travel the same distance, respectively, through leaves $4a$ or $4b$ as beam R travels through leaf $4b$ before it is completely absorbed or attenuated at 20, can require a considerable addition to the total width of the leaves. In the illustration of FIG. 2, this added width could be almost twice the minimum width required for absorption of the beam at beam path R passing through the solid portion of the leaf, i.e., not at a joint. As a result, in this prior art construction, beam paths $R_1$ and $R_2$ are shown as passing completely through leaves $4a$ and $4b$ at the joint, i.e., penetrating through the collimator, a highly undesirable condition.

It will also be apparent, for example, by examining the respective joints formed by closed leaves $4a-6a$, $4b-6b$, and $4p-6p$, that the same problem of penetration of the particle beam can result at the intersection of the respective opposing leaves in the two stacks when the leaves are in a closed position, i.e., abutting one another. While such end edges may also be formed with mating sawtooth surfaces, the same problem of maximizing the pathway of the particle beam through the shielding material occurs, resulting in the same need for added width of the leaves.

The addition of further width to the leaves, however, to prevent such unwanted penetration, either between adjacent leaves in the same stack, or through the joint created between opposing leaves in the closed position, results in added weight for each leaf. Since there must be a number of such leaves in order to provide sufficient resolution of the pattern to be outlined by the adjustable leaves, such added width of each individual leaf can add considerable weight to the overall structure of the collimator. When it is considered further that it is desirable to be able to rotate the collimator so that the adjustment of the leaves may, in essence be along two axes, rather than only one (i.e., in the plane normal to the beam path), the weight lo considerations are even further impacted by the width of the individual leaves, since added weight requires the provision of a more rugged rotational means as well.

It would, therefore, be desirable to provide an optimization of the width of the individual leaves of the collimator without, however, jeopardizing the penetration of the particle beam through the collimator at the joints between adjacent or opposing leaves.

SUMMARY OF THE INVENTION

It is, therefore, an object of this invention to provide a method for selecting an optimum width for the leaves of a collimator which will minimize the weight of each leaf while still providing adequate shielding in the sawtooth joints between adjacent leaves from penetration by the radiation beam.

In accordance with the invention, the width of a individual leaf in a collimator is selected to comprise the sum of the penetration depth or range of the particular type of radiation, e.g., particles, comprising the radiation beam in the particular material used for forming the leaf; plus the total path length across all the air gaps in the area defined between lines drawn across the peaks of adjacent sawtooth edges; plus at least one half of the length or period of a single sawtooth.

BRIEF DESCRIPTION OF THE DRAWINGS

FIG. 3 is a fragmentary end section view of two leaves in a stack of leaves in a collimator somewhat similar to one of the stacks of leaves shown in FIG. 1, except that the sawtooth joint in FIG. 3 is formed in accordance with the invention, showing the passage of radiation beams, such as particle beams, respectively into a solid portion of one of the leaves and partially through the leaves at the sawtooth joint between two adjacent leaves.

FIG. 4 is a fragmentary top view of a collimator showing the respective end edges of the top leaves in both stacks with the mating sawtooth end edges formed in accordance with the invention as shown in FIG. 3.

FIG. 5 is a flow sheet illustrating the process of the invention.

DETAILED DESCRIPTION OF THE INVENTION

Figure 1:
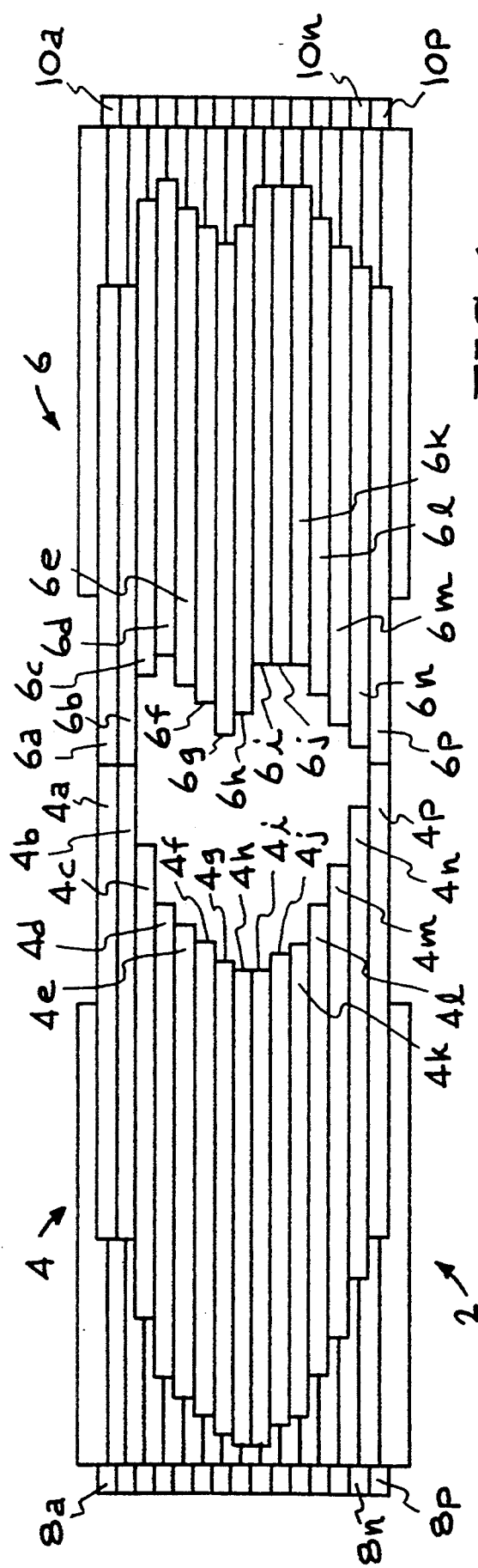
FIG. 1 is a side section view of a prior art collimator having individually adjustable leaves to permit formation of a variety of shaped openings through which a radiation beam, such as a particle beam, may pass.
Figure 2:
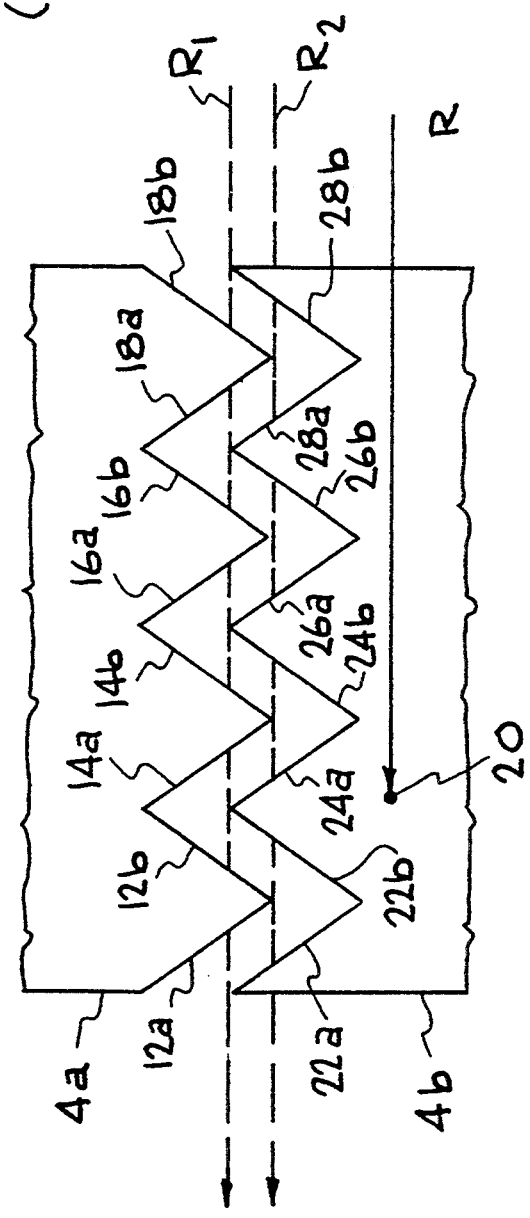
FIG. 2 is a fragmentary end section view of two leaves in one of the stacks of leaves shown in FIG. 1, showing the passage of radiation beams, such as particle beams, respectively into a solid portion of one of the leaves and through the leaves at the sawtooth joint between two adjacent leaves in a prior art construction of such a sawtooth joint.

The invention comprises a method for selecting the minimum width of individual leaves of a collimator having sawtooth top and bottom surfaces between adjacent leaves of a first stack of leaves and sawtooth end edges which are capable of intermeshing with the corresponding sawtooth end edges of leaves in a second stack of leaves of the collimator.

In accordance with the invention, the minimum width of individual leaves in the collimator, each having a sawtooth configuration in the surface facing another leaf in the same stack and a sawtooth end edge, is selected to comprise the sum of the penetration depth or range of the particular type of radiation comprising the beam in the particular material used for forming the leaf; plus the total path length across all the air gaps in the area of the joint at the edges between two leaves defined between lines drawn across the peaks of adjacent sawtooth edges; plus at least one half of the length or period of a single sawtooth. To accomplish this, in accordance with the method of the invention, the penetration depth of the particular type of radiation in the particular material to be used for the collimator leaf is first measured. Then the distance or gap between adjoining or abutting leaves is selected, and the ratio of this distance to the height of the sawteeth is selected. Finally the number of air gaps through which the radiation will pass between sawteeth is determined by selecting the number of sawteeth to be formed in the joint. The measurement and/or selection of these parameters will permit one to determine the minimum width of the leaf which is required to prevent passage of the beam through the sawtooth joint.

The type of collimator toward which the method of the invention is directed is a multileaf collimator in which each leaf in two parallel stacks is independently adjustable and where the joints formed by the adjoining surfaces of the leaves in the same stack, and the abutting end edge of the leaves in the respective stacks, are formed with sawtooth edges to inhibit the passage of radiation through such joints.

As shown in FIG. 3, stacked leaves 30a, 30b, and 30c are formed with sawtooth configurations on the surfaces thereon facing one another. Mating sawtooth surfaces 32 and 34, formed respectively on the surfaces of leaves 30a and 30b facing one another, and mating sawtooth surfaces 36 and 38, formed respectively on the surfaces of leaves 30b and 30c facing one another, are gapped at a predetermined distance and provided with a sufficient number of teeth, as will be explained below, so that a beam of radiation passing through the sawtooth joint formed by such surfaces along beam path R3, does not penetrate through the leaves, but rather stops at the point indicated at 40 in FIG. 3.

It should be noted that while isosceles triangles are shown in FIG. 3 for the cross sectional shape of the sawteeth, the two sides of the triangular sawtooth need not be equal. It should also be noted that the two sides of the sawtooth need not terminate at a point. In fact matching curved surfaces could be used instead. However, from a standpoint of ease of construction, i.e., machining, it will be preferable to lo construct the sawteeth surfaces having equal dimensions, i.e., as isosceles triangles in cross section.

In FIG. 4, the sawtooth end edge 31 of leave 30a and mating sawtooth end edge 51 of leave 50a are illustrated. The configuration of these surfaces can be identical to the mating sawtooth surfaces 32, 34, 36, and 38 shown in FIG. 3, and the discussion of the parameters used in the formation of the sawtooth surfaces of FIG. 3, in accordance with the invention to provide the minimum width for each leaf are equally applicable to the end edge sawteeth as well.

FIG. 4 further shows the positional relationship of the collimator to the radiation source and the patient, as well as illustrating the means for moving leaf 30a via DC motor means 60. FIG. 4 further shows the suspension of leaf 30 on pins 62 which fit into grooves (not shown) on the side surfaces of leaf 30a and which pins turn on roller bearings 64 which are mounted in frame 100 of the collimator to thus permit sliding movement of the collimator leaves.

Turning now to FIG. 3, in accordance with the invention, the minimum width W for the individual leaf may be expressed by the following formula:

(1) $W = R + A + L/2$ where:

R is the range or penetration depth of the particular radiation beam, e.g., particle beam in the particular material used for the leaf;

A is the total path length of the beam in air through the sawtooth joint;

L is the length of each sawtooth base (length of period).

The value of R will depend upon both the mass and energy of the particular particle as well as the material used to construct the leaves. Steel will probably be the material of choice from the standpoint of cost, strength, and roach inability. However, higher absorption would be possible by substitution of a material such as tungsten, while lighter weight could be achieved by using aluminum, at least for low energy beams.

The total path length A in equation (1) above for the travel of the beam through air, hypothetically traversing the complete width of the sawtooth joint, may be further expressed as follows:

(2) $A = an = a(2W)/L$ where:

a is the path length across a single air gap;

n is the total number of air gaps, which is related to the minimum width W for the individual leaf and the length L of each sawtooth base by the following equation:

(3) $n = 2W/L$

The path length a across a single air gap may be expressed as the ratio of the gap G with the tangent of angle $\theta$ shown in FIG. 3 as follows:

(4) $a = G/\tan\theta = G/(2H/L) = GL/2H$ wherein:

G is the gap or average distance between the surfaces of the leaves;

H is the height (valley to peak distance) of each sawtooth.

Then substituting GL/2H for a and 2W/L for n in equation (2), the value of A becomes:

(5) $A = [(GL)/2H]*[(2W)/L] = (GW)/H = W(G/H)$

As can be seen from equation (5), A, the total path length of the beam in air, is independent of the base length L of each sawtooth, but is determined by the product of the width W of the leaf with the ratio of the gap G to the height H of the sawtooth, i.e., $A = W(G/H)$. Substituting in equation (1) above for A the value W(G/H), and for L the value 2W/n (from equation (3) above), and solving for W, the minimum width W of the leaf may be expressed as:

(6) $W = R/(1 - G/H - 1/n)$

W in equation (6) above depends on the ratio r of the gap G to the height H. Substituting r = G/H, equation (6) may be rewritten as:

(7) $W = R/(1 - r - (1/n))$

Thus, the minimum width W can be calculated from equation (7) once R is known and the optimum values for r and n have been determined (or selected). Therefore, to determine the minimum value for the width W of each individual leaf in the collimator, to ensure that the beam will not penetrate through the sawtooth joint between adjacent or abutting leaves, using the above equations, one first measures the extent or distance of the penetration of the particular radiation beam into the material be used in constructing the collimator leaf to determine the value of R in equation (1) above.

Then one selects the gap distance G between the leaves, i.e., between adjacent leaves in the same stack or between the end edges of respectively abutting leaves in both stacks, as shown in FIG. 4. This value will be kept as small as possible within the tolerances needed to permit independent movement of each leaf without the generation of friction or drag by contact between the surfaces of adjacent leaves. Preferably, this value will range from about 0.1 millimeter (mm.) to about 0.5 mm.

Based on the selected value of the gap G, one selects a value for the height H of the sawtooth as ranging from at least 2 G to as high as 10 G. The choice is guided by the mechanical tolerances, i.e., variation in the gap G during use of the device, and ease of fabrication.

Finally one determines the value of n, the number of air gaps, which, in turn, is twice the number of saw teeth. This value, in turn, will be selected based on the economics of providing such corrugated surfaces on both surfaces, as well as the inner edge of each leaf in both stacks of leaves in the collimator. Furthermore, it will be noted from the examples given above, that there is a diminishing return in savings in leaf width as the number of saw teeth increase. Thus, while the minimum required width of the leaf decreases by about 25%, when the number of sawteeth is increased from 2 to 5 (n=0), the minimum required width W of the leaf only decreases about another 7% when the number of sawteeth is doubled from 5 to 10 (n=20). Still further increasing the number of saw teeth to 20 (n=40), would only decrease the value of W by about another 3%, while greatly increasing the cost of manufacture of the leaf.

The value of n should be at least about 4, and more preferably larger than 10. The maximum value of n (from a standpoint of economics versus added reduction in leaf width), however, should be about 20, although it is recognized that this number may be made higher if economically feasible.

With these values of R, r, and n, one can then determine the desired minimum width W of the collimator leaf in equation (7) above, in accordance with the invention.

Thus, the method of the invention provides the means for selecting values for the number of sawteeth, the gap between adjoining sawteeth, as well as the preferred relationship between the gap and the height of the individual sawteeth which, when coupled with the measured penetration of the particular radiation beam into a solid portion of the particular material to be used for the leaf, will enable one to minimize the width of each leaf while ensuring that radiation from the beam does not penetrate the collimator at the sawteeth joints separating adjoining or abutting leaves from one another so that the radiation will only pass through the collimator in the desired spatial pattern defined by the position of the leaves in the collimator. In this manner, cost, space and weight consideration may be minimized while still providing for the safety of the patient being subjected to the radiation treatment.

Having thus described the invention what is claimed is:

1. A method for selecting the minimum width of a metal leaf in an adjustable metal leaf collimator needed to prevent penetration of a particle beam of radiation completely through a sawtooth joint formed between adjacent or abutting leaves in the collimator which comprises measuring the penetration of said particle beam into a solid portion of the leaf, and determining the minimum width of the leaf as the sum of said measured penetration of said particle beam plus the length of the path of said particle beam through air in the spaces between the sawteeth plus at least one half the length of a single sawtooth period.

2. The method of claim 1 wherein said method of determining said minimum width of said metal leaf further is expressed by the equation: $W = R + A + \frac{1}{2}L$, where W is the width of said metal leaf, R is the penetration of said particle beam through said solid portion of said metal leaf, A is the total length of said particle beam path through air between the sawteeth, and L is the length of said single sawtooth period.

3. A method for selecting the minimum width of a leaf needed to prevent penetration of a particle beam of radiation completely through a sawtooth joint formed between adjacent or abutting leaves in an adjustable leaf collimator, where said leaf width=W, and $W = R + A + \frac{1}{2}L$ which comprises the steps of:
   a) measuring the penetration depth R in said leaf of said particle beam into a solid portion of said leaf;
   b) determining the length A of the path through air in the spaces between the sawteeth, where $A = a \times n$, n=twice the number of sawteeth, and $a = GL/2H$, where G is the gap between adjoining surfaces of the leaves, L is the length of the base of the sawtooth, and H is the height of a sawtooth, by:
      i) selecting the number of sawteeth to be formed along the width of the leaf; and
      ii) selecting the distance G between adjoining leaves;
      iii) selecting the value of H from a ratio of G to H within a range of H=2G to H=10G, and
   c) then adding to the sum of R+A at least one half the length L of a single sawtooth period to determine said minimum width of said leaf needed to prevent said penetration of said particle beam of radiation through said sawtooth joint.

4. The method of claim 3 wherein each of said leaves in said leaf collimator is a metal leaf.

5. The method of claim 4 wherein each of said metal leaves in said metal leaf collimator is a steel leaf.

6. The method of claim 4 wherein each of said metal leaves in said metal leaf collimator is a tungsten leaf.

7. The method of claim 4 wherein each of said metal leaves in said metal leaf collimator is an aluminum leaf.

8. A method for selecting the minimum width of a metal leaf in an adjustable metal leaf collimator needed to prevent penetration of a particle beam of radiation completely through a sawtooth joint formed between adjacent or abutting leaves in the collimator which comprises measuring the penetration of said particle beam through a solid portion of said metal leaf, and determining the minimum width of said metal leaf, using the formula:

$$W = R/(1 - G/H - 1/n)$$

where: R is the penetration of said beam into said solid portion of said metal leaf;
   G is the gap between the sawtooth surfaces adjacent or abutting leaves forming the joint;
   H is the height of the individual sawtooth; and
   n is twice the number of sawteeth on each metal leaf in the joint.

9. The method of claim 8 which further comprises selecting the value of said gap G between said sawtooth surfaces of said adjacent or abutting leaves.

10. The method of claim 5 which further comprises selecting a height H for each sawtooth which ranges from about 2 to about 10 times the value of G.

11. The method of claim 8 which further comprises selecting a value for n which equals at least 4.

* * * * *